United States Patent [19]

Rei et al.

[11] Patent Number: 5,102,657
[45] Date of Patent: Apr. 7, 1992

[54] MICROBIOCIDAL COMPOSITIONS

[75] Inventors: Nuno M. Rei, Boxford; Lawrence P. Grant, Danvers, Mass.

[73] Assignee: Morton International, Inc., Chicago, Ill.

[21] Appl. No.: 630,373

[22] Filed: Dec. 18, 1990

Related U.S. Application Data

[63] Continuation of Ser. No. 255,796, Oct. 11, 1988, abandoned.

[51] Int. Cl.$^5$ .................... A61K 31/10; A61K 31/74
[52] U.S. Cl. .................... 514/504; 424/486; 523/122
[58] Field of Search .............. 424/78, 486; 514/504; 523/122

[56] References Cited

U.S. PATENT DOCUMENTS

| | | | |
|---|---|---|---|
| 3,360,431 | 12/1967 | Yeager | 424/419 |
| 3,755,224 | 8/1973 | Lutz, Jr. | 252/182 |
| 3,890,270 | 6/1975 | Minieri | 523/122 |
| 4,416,975 | 11/1983 | Green | 430/270 |
| 4,761,247 | 8/1988 | Rei et al. | 514/504 |

FOREIGN PATENT DOCUMENTS

| | | |
|---|---|---|
| 1174804 | 9/1984 | Canada . |
| 56-81373 | 3/1981 | Japan . |
| 1031524 | 6/1966 | United Kingdom . |

*Primary Examiner*—Lester L. Lee
*Assistant Examiner*—E. J. Kraus
*Attorney, Agent, or Firm*—Herbert W. Larson; Gerald K. White

[57] ABSTRACT

Homogeneous, stable liquid compositions are provided comprising a carrier, e.g., a plasticizer, a solvent selected from $C_5$ to $C_9$ aliphatic alcohols and diols, e.g., isodecyl alcohol, 2-ethyl hexanol, 2-ethyl-1, 3-hexanediol or mixtures thereof, and a microbiocidal compound soluble in said solvent wherein the microbiocidal compound is present in amounts greater than 2.5 percent by weight of the combined weight of carrier, solvent and microbiocidal compound.

13 Claims, No Drawings

MICROBIOCIDAL COMPOSITIONS

This application is a continuation of 07/255,796, filed Oct. 11, 1988, now abandoned.

BACKGROUND OF THE INVENTION

1. Field of the Invention

This invention relates to homogeneous compositions comprising a carrier, a microbiocidal compound, and a solvent for the microbiocidal compound which is also compatible with the carrier.

The present invention further relates to a process for imparting microbiocidal properties to polymer compositions comprising adding to the polymer composition a homogeneous microbiocidal composition comprising a carrier, a microbiocidal compound, and a solvent for the microbiocidal compound.

This invention further relates to compositions comprising a homogeneous solution of a liquid plasticizer for vinyl resins, a biologically effective amount of a microbiocidal compound, and a solvent for the microbiocidal compound.

This invention further relates to polymer. e.g.. vinyl resin, compositions comprising an admixture of a polymer and a composition containing a carrier, e.g., plasticizer, and in an amount sufficient to impart microbiocidal properties to the polymer composition, a microbiocidal compound dissolved in a solvent.

2. Prior Art

It is presently common practice to protect polymer or plastic compositions from microbiological, e.g.. bacterial or fungal attack by incorporating microbiocidal compounds into the polymer or plastic compositions. The resulting polymer compositions prevent the deterioration of articles formed from the polymer compositions which is due to microbiological attack on the polymer, the plasticizers or other polymer additives which are normally incorporated into the polymer compositions to impart desirable physical properties to the articles and to facilitate forming of the articles.

Many of the available microbiocidal materials are solid, and in order to incorporate them homogeneously into polymer compositions, it is necessary to first mix them with liquids which solubilize or disperse the microbiocidal materials uniformly and, thereafter, mix the thus-formed liquid compositions with the polymers. Unfortunately, the solubilities of many of the microbiologically active compounds in the more common solvents are quite low. Therefore, it is either difficult to incorporate a sufficiently high concentration of a microbiocidal compound with a polymer or, if a sufficiently high concentration of the microbiocidal compound can be incorporated in the polymer, an undesirably high concentration of the solvent must also be incorporated into the polymer, compromising the desirable characteristics of the polymer composition.

Attempts to solve these problems have met with varying, often limited, success. For example, U.S. Pat. No. 3,288,674 issued Nov. 29. 1966 to Yeager (reissued on Sept. 20, 1977 as Re. 29,409), U.S. Pat. No. 3,360,431 issued Dec. 26, 1967 to Yeager, and U.S. Pat. No. 3,689,449 issued Sept. 5, 1972 to Yeager and Wilson disclose the use of solvents having a labile hydrogen, such as phenols (e.g. nonyl phenol) and $C_5$–$C_{12}$ aliphatic alcohols, to dissolve microbiocidally active phenoxarsine compounds, the resulting solutions being subsequently incorporated into polymeric resin compositions. While the $C_5$–$C_{12}$ aliphatic alcohols were found to be useful as solvents for the phenoxarsines, their ability to aid in the incorporation of the phenoxarsines into plasticizer compositions was recognized only to a limited extent. Thus, the maximum amount of phenoxarsine disclosed as being incorporated into a plasticizer composition is only 2.5 percent by weight (based on the total weight of phenoxarsine, solvent, and plasticizer).

U.S. Pat. No. 4,663,077 issued May 5, 1987 to Rei and Wilson describes the advantageous use of aryl alkanols, such as benzyl alcohol, as solvents for microbiocidal agents which are to be formulated into solutions with carriers, such as plasticizers and/or other processing aids. The patent teaches that aryl alkanol solvents, such as benzyl alcohol, increase the levels of microbiocides, particularly phenoxarsines, which can be dissolved per amount of solvent.

U.S. Pat. No. 4,049,822 issued Sept. 20, 1977 to Rei et al. discloses that phenoxarsines can be solubilized with glycyl phosphites or glycyl phosphonates. These phosphites and phosphonates may be used in admixture with solvents having a labile hydroxyl group, such as phenols and $C_5$–$C_{12}$ aliphatic alcohols.

SUMMARY OF THE INVENTION

In accordance with the present invention, there are provided homogeneous, stable liquid compositions comprising a carrier, a solvent selected from $C_5$ to $C_9$ aliphatic alcohols and diols and a microbiocidal compound soluble in said solvent wherein the microbiocidal compound is present in the composition as a solute in the solvent and constitutes greater than 2.5 percent by weight of the combined weight of the carrier, solvent and microbiocidal compound.

Also provided in accordance with this invention is a process for imparting microbiocidal properties to a polymer composition comprising adding to a polymer, in an amount at least sufficient to impart antimicrobial properties to the polymer composition, a homogeneous, stable liquid composition comprising a carrier, a solvent selected from $C_5$ to $C_9$ aliphatic alcohols and diols, and a microbiocidal compound soluble in said solvent, wherein the microbiocidal compound is present in the composition as a solute in the solvent and constitutes greater than 2.5 percent by weight of the combined weight of the carrier, microbiocidal compound and solvent.

There are further provided in accordance with the present invention polymer. e.g., vinyl resin, compositions comprising an admixture of a polymer and, in an amount at least sufficient to impart antimicrobial properties to the polymer composition, a homogeneous, stable liquid composition comprising a carrier, e.g.. a plasticizer for the polymer, a solvent selected from $C_5$ to $C_9$ aliphatic alcohols and diols, and a microbiocidal compound soluble in said solvent, wherein the microbiocidal compound is present as a solute in the solvent and constitutes greater than 2.5 percent by weight of the combined weight of carrier, microbiocidal compound, and solvent.

DESCRIPTION OF THE PREFERRED EMBODIMENTS

The present invention is specifically directed to applications in which the microbiocidal compound is not sufficiently in a carrier, such as a plasticizer or other processing aid, to be provided to the resin through solution in the carrier alone. In such case, an organic solvent is used which is a cosolvent for the microbiocidal compound and the resin or a cosolvent for the microbiocidal compound and the carrier, e.g.. the plasticizer. Specifically, the present invention is directed to applications in which the cosolvent is a $C_5$ to $C_9$ aliphatic alcohol or diol such as isodecyl alcohol. 2-ethyl hexanol, 2-ethyl-1, 3-hexanediol or mixtures thereof which have been found to allow the addition of relatively high levels of microbiocidal compounds to a carrier, e.g., plasticizer, and provide homogeneous, stable compositions. As used herein, the term "stable" means that the microbiocide remains dissolved in the carrier-containing composition and does not precipitate or recrystallize after standing at room temperature for, e.g., 30 days, or after being subjected to several freeze/thaw cycles.

As used herein, the term "$C_5$ to $C_9$ aliphatic alcohols or diols" refers to compounds whose longest continuous chain of aliphatic carbon atoms has from 5 to 9 carbon atoms in it, and with one or two —OH groups being bonded to that $C_5$ to $C_9$ chain. Thus, the overall molecule may contain greater than nine carbon atoms, without departing from this definition, as long as the longest continuous chain of carbon atoms is $C_5$ to $C_9$ An example of such a compound is isodecyl alcohol which has 10 carbon atoms overall, but only nine carbon atoms in its longest continuous chain.

Examples of the $C_5$ to $C_9$ aliphatic alcohols and diols of this invention include, but are not limited to, isodecyl alcohol (including the material commonly termed "isodecyl alcohol" which is a mixture principally of trimethyl heptanols), 2-ethyl hexanol and 2-ethyl-1, 3-hexanediol.

Examples of the types of microbiocidal compounds which may be employed in this invention include, but are not limited to, phenoxarsines (including bisphenoxarsines), and phenarsazines (including bisphenarsazines).

The microbiocidal phenoxarsine and phenarsazine compounds useful in the compositions of this invention include compounds represented by the formulas:

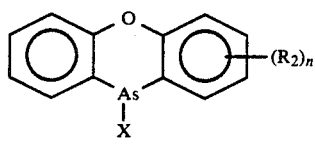

and

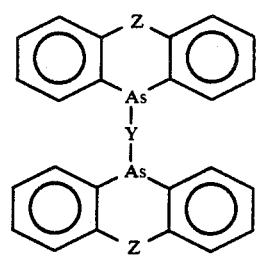

where X is thiocyanate, Y is oxygen or sulfur, Z is oxygen or nitrogen, R is halo or lower alkyl, and n is 0 to 3. Examples of these phenoxarsines and phenarsazines include, but are not limited to, 10,10'-oxybisphyenoxyarsine (OBPA); 10-thiocyanato phenoxarsine; 10,10'-thiobisphenoxarsine; 10,10'-oxygisphenarsazine and 10,10'-thiobisphenarsazine.

The most preferred microbiocidal compounds are the bisphenoxarsines and bisphenarsazines having the formula:

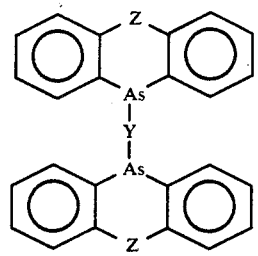

where Y is oxygen or sulfur and Z is oxygen or nitrogen. Of these bisphenoxarsines and bisphenarsazines, the most preferred are 10,10'-oxybisphenoxarsine; 10,10'-thiobisphenoxarsine; 10,10'-oxybisphenarsazine; and 10,10'-thiobisphenarsazine.

The microbiodical compositions useful in this invention should be employed in an amount at least sufficient to impart microbiocidal properties to the polymer composition or material containing them. This amount can vary widely depending upon the particular microbiocidal compound employed, the other components of the polymer composition in which it is employed, the environment in which the polymer composition will function, and several other factors. The minimum amount of microbiocidal compound employed in a polymer composition is determined by what is known in the art as its Minimum Inhibitory Concentration (MIC). The maximum amount of microbiocidal compound which can be employed in a polymer composition is determined only by the amount of microbiocidal compound which can be uniformly incorporated into a particular polymer composition without adversely affecting the physical properties of the polymer composition. In general, the polymer compositions of this invention which possess microbiocidal properties contain from about 50 parts per million (ppm) to about 10,000 ppm, preferably about 100 ppm to 500 ppm, of microbiocidal compound, phenoxarsine and phenarsazine compounds the preferred microbiocidal compounds in accordance with this invention, are used at levels of between about 100 and about 5,000 ppm (based upon the total weight of the polymer composition) and preferably between about 300 and about 1,000 ppm.

The microbiocidal compositions of this invention preferably contain much more microbiocidal compound than would be necessary simply to impart the desired microbiocidal properties to them. These compositions preferably contain large amounts of microbiocidal compound because they are advantageously employed as "concentrates" to produce polymer compositions which have lower concentrations of microbiocidal compounds, but still have the desired degree of microbiocidal activity. For example, a carrier-containing liquid composition may contain about 5% to about 10% microbiocidal compound, but may in turn, be used to prepare a polymer composition containing only 100 to 500 ppm microbiocidal compound.

The microbiocidal compositions of this invention, comprising a carrier, a solvent selected from $C_5$ to $C_9$ aliphatic alcohols and diols such as isodecyl alcohol, 2-ethyl hexanol. 2-ethyl-1, 3-hexanediol or mixtures thereof, and a microbiocidal compound, may be employed as additives for polymer compositions to impart microbiocidal properties to the polymer compositions. Examples of suitable carriers include, but are not limited to, plasticizers, and lubricants. Specific examples of carriers include, but are not limited to, typical plasticizers such as tricresyl phosphate, dipropylene glycol dibenzoate, diphenylcresyl phosphate, epoxidized soya, epoxidized tallate, dioctyl azelate, di(2-ethyl hexyl) phthalate, alkyl aryl phosphates, diisobutyl phthalate, diisodecyl phthalate, hydrogenated methyl rosin ester n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, trioctyl trimellitate and low molecular weight polymeric plasticizers, such as paraplex G-30 ® plasticizer sold by Rohm & Haas Co., and the like. Of these plasticizers di(2-ethyl hexyl) phthalate, diisodecyl phthalate, butyl benzyl phthalate and epoxidized soya are preferred. Other polymer processing aids useful as carriers in accordance with this invention include, but are not limited to, polypropylene glycol; 1,4-butanediol; and methyl ethyl ketone. The compositions of this invention may be added either directly to the polymer composition or they may be first incorporated into an additional amount of carrier, and then incorporated into the polymer composition. When the latter manner is chosen, the carrier may be any of a variety of materials including the carriers identified above, which are compatible with the polymeric resin and microbiocidal composition, i.e., the microbiocidal compound does not precipitate or otherwise separate from the cosolvent when incorporated into a polymeric resin along with the carrier.

It is generally a problem to solubilize sufficiently high concentrations of commonly used microbiocides in solvents, and have the resulting solution remain stable when added to a carrier. e.g.. plasticizer. Generally, the solvent used to carry the microbiocidal compound into the carrier-containing concentrate composition and into the polymeric resin serves little or no beneficial function in the final polymeric composition and may even be detrimental if present in too high a concentration. The concentrate composition should contain the correct amount of microbiocide so that when the carrier, e.g., plasticizer, is employed at optimal amounts, the carrier containing concentrate composition provides the correct amount of microbiocidal compound to the end-use polymer composition. At the other extreme, a solution should not be too highly concentrated in microbiocidal compound, lest mixing problems be encountered; however, with the case of most microbiocides, obtaining a sufficiently high concentration of microbiocides is the major problem. For example, using solvents such as nonyl phenol, it was, heretofore, difficult to provide concentrate compositions which contained more than 2% OBPA by weight. When one considers that only a given amount of any carrier, such as a plasticizer, might be incorporated into a polymeric composition, if such a concentrate were the only source of microbiocidal compound to the final polymer composition, the microbiocide might be incorporated into the polymer composition only at sub-optimal levels. Using solvents having aryl alkanol moieties as described above, OBpA-containing plasticizing compositions containing 5% and upwards by weight have been produced. It has now been found that using $C_5$ to $C_9$ aliphatic alcohols or diols such as isodecyl alcohol, 2-ethyl hexanol, 2-ethyl-1, 3-hexanediol or mixtures thereof as the solvent likewise allows one to prepare concentrates containing higher amounts. e.g., 5% to 10% by weight, of the microbiocide. e.g., OBpA.

High concentrations of microbiocide compounds, both in solutions and in carrier-containing concentrate compositions, are desirable in other ways too. Less material, e.g., solvent, is required. Shipping and handling cost savings are also realized because less material must be shipped and stored.

The polymers employed in the processes and products of this invention cover a wide variety of materials. In general, they include thermoplastic and thermosetting polymers. elastomers, and other materials commonly known as "plastics". Other organic materials, for instance, naturally occurring materials, such as natural rubbers, cellulose and the like, are considered full equivalents of the "polymers" of this invention and should be included within that term. Examples of the polymers useful in the practice of this invention include, but are not limited to vinyl resins (such as those made from vinyl chloride and/or vinyl esters), polyolefins (such as polyethylene and polypropylene), elastomeric polyurethanes, nylon, polystyrene, polyesters (such as polyethylene terephthalate), polycarbonates, acrylonitrile-butadiene-styrene (ABS) copolymers, SBR rubbers, styrene-acrylonitrile copolymers, acrylic polymers, thermosetting polyurethanes (such as those used for foams and coatings), phenolic resins, silicone rubbers, natural rubber, EDPM polymers, cellulose and its derivatives, epoxy resins, and various latexes.

The microbiocidal compositions of this invention can be prepared by simply adding the desired amount of microbiocidal compound to the solvent, heating (if necessary) the resulting mixture to a temperature which will cause the microbiocidal compound to dissolve, and maintaining that temperature until all of the microbiocidal compound dissolves. The resulting solution can then be cooled to room temperature. In this manner, stable microbiocidal solutions, i.e., those wherein no significant amount of microbiocidal compound precipitates from the solution upon cooling to room temperature, can be formed. The carrier-containing compositions of the present invention may then be prepared by merely adding the carrier to the microbiocidal solution, prepared as described above, and mixing at room temperature until a uniform solution results. Alternatively, all ingredients of the carrier-containing composition (microbiocidal compound, solvent and carrier) can be mixed together and heated (if necessary) until the microbiocidal compound dissolves.

The microbiocidal compositions of this invention can be used to impart microbiocidal properties to polymer compositions. This can be done by simply adding the carrier-containing microbiocidal composition to the polymer composition by any of several convenient methods known in the art. Thus, for instance, the polymer resin can be melted and the microbiocidal carrier-containing composition added to and mixed with it (as in an extruder). Alternatively, the polymeric resin can be softened with or dissolved in a solvent and the microbiocidal carrier-containing composition added to and mixed therewith.

The following examples illustrate the present invention, and are not intended to limit the invention or its scope in any manner. As used in the examples and throughout this specification, all parts and percentages are by weight unless otherwise indicated.

EXAMPLE 1

A solution containing 20 wt % OBPA dissolved in 80 wt % isodecyl alcohol (IDA), the percentages based on total solution weight, was prepared by mixing the ingredients and heating the resulting mixture to about 220° F. and maintaining that temperature until all of the OBPA dissolved. The resulting solution was stable, but crystallized after 24 hours. Portions of this solution were then used to prepare carrier-containing compositions containing 5 wt % OBPA using the carriers (plasticizers) listed in Table 1 below wherein the numbers indicate the weight percent of each ingredient based on total composition weight. These carrier-containing compositions were prepared by diluting the OBPA/IDA solution with the carrier and mixing the resulting product.

TABLE 1

| Sample | OBPA | IDA | DINP[1] | DOP[2] | DIDP[3] | S-160[4] | ESO[5] | S-711[6] | Silicone Oil |
|---|---|---|---|---|---|---|---|---|---|
| 1 | 5 | 20 | 75 | | | | | | |
| 2 | 5 | 20 | | 75 | | | | | |
| 3 | 5 | 20 | | | 75 | | | | |
| 4 | 5 | 20 | | | | 75 | | | |
| 5 | 5 | 20 | | | | | 75 | | |
| 6 | 5 | 20 | | | | | | 75 | |
| 7 | 5 | 20 | | | | | | | 75 |

[1]DINP is diisononyl phthalate
[2]DOP is di(2-ethyl hexyl) phthalate, sometimes called dioctyl phthalate
[3]DIDP is diisodecyl phthalate
[4]S-160 is butyl benzyl phthalate
[5]ESO is epoxidized soya
[6]S-711 is a mixture of $C_7$, $C_9$ and $C_{11}$ branched phthalates.

The stability of Samples 1–7 was determined with the results indicted in Table 2.

TABLE 2

| Sample | Carrier | Immediately After Preparation | After 1 Day At Room Temp | After 1 Month At Room Temp | After 5 Freeze/Thaw Cycles |
|---|---|---|---|---|---|
| 1 | DINP | OK | OK | OK | OK |
| 2 | DOP | OK | OK | OK | OK |
| 3 | DIDP | OK | OK | OK | OK |
| 4 | S-160 | OK | OK | OK | OK |
| 5 | ESO | OK | OK | OK | OK |
| 6 | S-711 | OK | OK | OK | OK |
| 7 | Silicone Oil | OK | OK | NG* | NG |

*NG = unstable, precipitate formed

All of the samples exhibited good stability throughout the room temperature aging and freeze/thaw cycling with the exception of Sample 7. That sample, which employed silicone oil as the carrier, was not as stable as the other samples after long term room temperature aging and freeze/thaw cycling.

EXAMPLE 2

Additional carrier-containing compositions were prepared in the manner described in Example 1 using the ingredients and amounts indicated in Table 3 below wherein the numbers indicate the weight percent of each ingredient based on total composition weight.

TABLE 3

| Sample | OBPA | IDA | ESO | DOP | DIDP | S-160 |
|---|---|---|---|---|---|---|
| 8 | 5 | 20 | 75 | — | — | — |
| 9 | 5 | 20 | — | 75 | — | — |
| 10 | 5 | 20 | — | — | 75 | — |
| 11 | 5 | 20 | — | — | — | 75 |
| 12 | 5 | 11.7 | 83.3 | — | — | — |
| 13 | 5 | 11.7 | — | 83.3 | — | — |
| 14 | 5 | 11.7 | — | — | 83.3 | — |
| 15 | 5 | 11.7 | — | — | — | 83.3 |
| 16 | 5 | 7.5 | 87.5 | — | — | — |
| 17 | 5 | 7.5 | — | 87.5 | — | — |
| 18 | 5 | 7.5 | — | — | 87.5 | — |
| 19 | 5 | 7.5 | — | — | — | 87.5 |
| 20 | 10 | 40 | 50 | — | — | — |
| 21 | 10 | 40 | — | 50 | — | — |
| 22 | 10 | 40 | — | — | 50 | — |
| 23 | 10 | 40 | — | — | — | 50 |
| 24 | 10 | 23.3 | 66.7 | — | — | — |
| 25 | 10 | 23.3 | — | 66.7 | — | — |
| 26 | 10 | 23.3 | — | — | 66.7 | — |
| 27 | 10 | 23.3 | — | — | — | 66.7 |
| 28 | 10 | 15 | 75 | — | — | — |
| 29 | 10 | 15 | — | 75 | — | — |
| 30 | 10 | 15 | — | — | 75 | — |
| 31 | 10 | 15 | — | — | — | 75 |

The stability of each of Samples 8–31 was determined with the results indicated on Table 4 below.

TABLE 4

| Sample | Carrier | Immediately after Preparation | On Cooling | After 1 Day at Room Temp | After 1 Month At Room Temp | After 5 Freeze/Thaw Cycles | 30 Days Heat Aging at 55° C. |
|---|---|---|---|---|---|---|---|
| Stability For 5% OBPA Formulation | | | | | | | |
| 8 | ESO | + | + | + | + | + | + |
| 9 | DOP | + | + | + | + | + | + |
| 10 | DIDP | + | + | + | + | + | + |
| 11 | S-160 | + | + | + | + | + | + |
| 12 | ESO | + | + | + | + | + | + |
| 13 | DOP | + | + | + | + | + | + |
| 14 | DIDP | + | + | + | + | + | + |
| 15 | S-160 | + | + | + | + | + | + |
| 16 | DSO | + | + | + | + | — | — |
| 17 | DOP | + | — | — | — | — | — |
| 18 | DIDP | + | + | + | + | + | + |
| 19 | S-160 | + | + | + | + | + | + |
| Stability For 10% OBPA Formulation | | | | | | | |
| 20 | ESO | + | + | + | + | + | + |

TABLE 4-continued

| Sample | Carrier | Immediately after Preparation | On Cooling | After 1 Day at Room Temp | After 1 Month At Room Temp | After 5 Freeze/ Thaw Cycles | 30 Days Heat Aging at 55° C. |
|---|---|---|---|---|---|---|---|
| 21 | DOP | + | + | + | + | + | + |
| 22 | DIDP | + | + | + | + | + | + |
| 23 | S-160 | + | + | + | + | + | + |
| 24 | ESO | + | + | + | + | + | + |
| 25 | DOP | + | + | + | + | + | + |
| 26 | DIDP | + | + | + | + | + | + |
| 27 | S-160 | + | + | + | + | + | + |
| 28 | ESO | + | + | + | + | + | + |
| 29 | DOP | + | + | — | — | — | — |
| 30 | DIDP | + | + | — | — | — | — |
| 31 | S-160 | + | + | + | + | + | + |

+ = Good Stability
— = Poor Stability recrystalization of OBPA

The above data indicates that most of the samples were stable. Some of the samples were not stable when relatively low amounts of IDA were employed, but were stable when the amount of IDA was higher, e.g., Sample 17 vs. Samples 9 and 13; ample 29 vs. Samples 21 and 25; and Sample 30 vs. Samples 22 and 26.

EXAMPLE 3

This example illustrates carrier-containing compositions of the present invention which contain microbiocides other than OBPA. These compositions were prepared in the manner described in Example 1 using the ingredients and amount indicated in Table 5 below wherein the numbers indicate the ht percent of each ingredient based on total composition weight.

TABLE 5

| Sample | Biocide | Biocide | IDA | Plasticizer |
|---|---|---|---|---|
| 32 | 10-CPA | 5 | 20 | 75 |
| 33 | RH-948 | 5 | 20 | 75 |
| 34 | Myacide AS | 5 | 20 | 75 |

10-CPA is 10-chloro-phenoxarsine.
RH-948 is n-cyclohexyl-4, 5-dichloro-4-isothiazolin-3-one
Myacide AS is 90% 2-bromo-2-nitropropane-1,3-diol, 10% inert ingredients The stability of Samples 32-34 was determined, and the results are indicated in Table 6 below.

TABLE 6

| Sample | Biocide | Carrier | Immediately after Preparation | On Cooling | After 1 Day at Room Temp | After 1 Month At Room Temp | After 5 Freeze/ Thaw Cycles | 30 Days Heat Aging at 55° C. |
|---|---|---|---|---|---|---|---|---|
| 32 | 10-CPA | DIDP | — | — | — | — | — | — |
| 33 | RH-948 | DIDP | + | + | + | + | + | + |
| 34 | Myacide AS | DIDP | — | — | — | — | — | — |

+ = Good Stability
— = Poor Stability recrystalization

The above results illustrate that not all microbiocides are soluble/stable in IDA to the same extent. Thus, 5% 10-CPA (a compound closely related to OBPA) would not dissolve in 20% IDA, and Myacide AS was not stable in the carrier-containing composition at the 5% level. However, under the same conditions, i.e.. 5% microbiocide and 20% IDA, RH-948 was very stable.

COMPARATIVE EXAMPLE A

This example illustrates carrier-containing compositions which were prepared from a 20% concentrate of OBPA in dodecyl phenol instead of IDA. These compositions were prepared in the manner described in Example 1 using the ingredients and amounts indicated in Table 7 below wherein the numbers refer to the weight percent of each ingredient based on total composition weight.

TABLE 7

| Sample | OBPA | DDP DOP | ESO | DINP | Silicone Oil | DIDP | S-711 | DOP | S-160 |
|---|---|---|---|---|---|---|---|---|---|
| A | 5 | 20 | 75 | — | — | — | — | — | — |
| B | 5 | 20 | — | 75 | — | — | — | — | — |
| C | 5 | 20 | — | — | 75 | — | — | — | — |
| D | 5 | 20 | — | — | — | 75 | — | — | — |
| E | 5 | 20 | — | — | — | — | 75 | — | — |
| F | 5 | 20 | — | — | — | — | — | 75 | — |
| G | 5 | 20 | — | — | — | — | — | — | 75 |
| H | 2 | 8 | 90 | — | — | — | — | — | — |
| I | 2 | 8 | — | 90 | — | — | — | — | — |
| J | 2 | 8 | — | — | 90 | — | — | — | — |
| K | 2 | 8 | — | — | — | 90 | — | — | — |
| L | 2 | 8 | — | — | — | — | 90 | — | — |
| M | 2 | 8 | — | — | — | — | — | 90 | — |
| N | 2 | 8 | — | — | — | — | — | — | 90 |
| O | 1 | 4 | 95 | — | — | — | — | — | — |
| P | 1 | 4 | — | 95 | — | — | — | — | — |

TABLE 7-continued

| Sample | OBPA | DDP DOP | ESO | DINP | Silicone Oil | DIDP | S-711 | DOP | S-160 |
|---|---|---|---|---|---|---|---|---|---|
| Q | 1 | 4 | — | — | 95 | — | — | — | — |
| R | 1 | 4 | — | — | — | 95 | — | — | — |
| S | 1 | 4 | — | — | — | — | 95 | — | — |
| T | 1 | 4 | — | — | — | — | — | 95 | — |
| U | 1 | 4 | — | — | — | — | — | — | 95 |

The stability of the 20% concentration solution and samples A-U was tested with the results indicated in Table 8 below.

TABLE 8

| 20% OBPA/DDP Concentrate Solution Stability | | | |
|---|---|---|---|
| Immediately After Preparation | After 1 Day at Room Temp | After 30 Days at Room Temp | After 5 Freeze/thaw Cycles |
| OK | OK | OK | OK |

| Carrier-containing composition stability | | | | | | |
|---|---|---|---|---|---|---|
| Sample | OBPA | Carrier | Immediately After Preparation | After 1 Day Room Temp | After 30 Days Room Temp | After 5 Freeze/Thaw Cycles |
| A | 5 | ESO | OK | NG | NG | NG |
| B | 5 | DINP | | | | |
| C | 5 | Silicone Oil | | | | |
| D | 5 | DIDP | | | | |
| E | 5 | S-711 | | | | |
| F | 5 | DOP | | | | |
| G | 5 | S-160 | | | | |
| H | 2 | ESO | OK | NG | NG | NG |
| I | 2 | DINP | | | | |
| J | 2 | Silicone Oil | | | | |
| K | 2 | DIDP | | | | |
| L | 2 | S-711 | OK | OK | NG | NG |
| M | 2 | DOP | OK | NG | NG | NG |
| N | 2 | S-160 | OK | OK | OK | NG |
| O | 1 | ESO | OK | NG | NG | OK |
| P | 1 | DINP | | | | |
| Q | 1 | Silicone Oil | | | | |
| R | 1 | DIDP | | | | |
| S | 1 | S-711 | OK | OK | OK | NG |
| T | 1 | DOP | OK | NG | NG | OK |
| U | 1 | S-160 | OK | OK | OK | OK |

The above data illustrates that, while the 20% concentrate solution of OBPA in dodecyl phenol is stable, with only a few exceptions, the carrier-containing compositions are unstable, even at the 1% OBPA level.

COMPARATIVE EXAMPLE B

Additional materials were tested in the same manner described in Comparative Example A using the ingredients and amounts indicated in Table 9 below wherein the numbers refer to weight percent of each ingredient based on total composition weight.

TABLE 9

| Sample | OBPA | MPBA | Polymeg | W-430 | MPT | EPAL | DIDP | S-160 | ESO |
|---|---|---|---|---|---|---|---|---|---|
| 1A | 2 | 8 | — | — | — | — | 90 | — | — |
| 2A | 2 | 8 | — | — | — | — | — | 90 | — |
| 3A | 2 | 8 | — | — | — | — | — | — | 90 |
| 4A | 5 | 20 | — | — | — | — | 75 | — | — |
| 5A | 5 | 20 | — | — | — | — | — | 75 | — |
| 6A | 5 | 20 | — | — | — | — | — | — | 75 |
| 1B | 2 | — | 8 | — | — | — | 90 | — | — |
| 2B | 2 | — | 8 | — | — | — | — | 90 | — |
| 3B | 2 | — | 8 | — | — | — | — | — | 90 |
| 4B | 5 | — | 20 | — | — | — | 75 | — | — |
| 5B | 5 | — | 20 | — | — | — | — | 75 | — |
| 6B | 5 | — | 20 | — | — | — | — | — | 75 |
| 1C | 2 | — | — | 8 | — | — | 90 | — | — |
| 2C | 2 | — | — | 8 | — | — | — | 90 | — |
| 3C | 2 | — | — | 8 | — | — | — | — | 90 |
| 4C | 5 | — | — | 20 | — | — | 75 | — | — |
| 5C | 5 | — | — | 20 | — | — | — | 75 | — |
| 6C | 5 | — | — | 20 | — | — | — | — | 75 |
| 1D | 2 | — | — | — | 8 | — | 90 | — | — |
| 2D | 2 | — | — | — | 8 | — | — | 90 | — |
| 3D | 2 | — | — | — | 8 | — | — | — | 90 |
| 4D | 5 | — | — | — | 20 | — | 75 | — | — |
| 5D | 5 | — | — | — | 20 | — | — | 75 | — |
| 6D | 5 | — | — | — | 20 | — | — | — | 75 |
| 1E | 2 | — | — | — | — | 8 | 90 | — | — |
| 2E | 2 | — | — | — | — | 8 | — | 90 | — |
| 3E | 2 | — | — | — | — | 8 | — | — | 90 |
| 4E | 5 | — | — | — | — | 20 | 75 | — | — |
| 5E | 5 | — | — | — | — | 20 | — | 75 | — |
| 6E | 5 | — | — | — | — | 20 | — | — | 75 |

MPBA is m-phenoxy benzyl alcohol
Polymeg is Polymeg 1000 poly (oxytetramethylene) diol
W-430 is Weston 430 Phosphite C which is tris(dipropyleneglycyl) phosphite
MPT is m-phenoxytoluene
EPAL is a mixture of high straight chain alcohols.

The stability of the carrier-containing compositions of Table 9 and the 20% concentrate solution was tested with the results indicated in Table 10 below.

TABLE 10

20% OBPA Concentrate Solution Stability

| Solvent | Immediately After Preparation | After 2 Weeks Room Temp | After 5 Freeze/Thaw Cycles | After 30 Days in Oven At 55° C. |
|---|---|---|---|---|
| MPBA | OK | OK | OK | OK |
| Polymeg | NG | NG | NG | NG |
| W-430 | OK | OK | OK | NG |
| MPT | NG | NG | NG | NG |
| EPAL | OK | NG | NG | NG |

Carrier-Containing Composition Stability

| Sample | | Immediately After Preparation | After 2 Weeks Room Temp | After 5 Freeze/Thaw Cycles | After 30 Days in Oven At 55° C. |
|---|---|---|---|---|---|
| 1A, 2A, 3A, 4A, 5A, 6A | (MPBA) | OK | OK | OK | OK |
| 1B, 2B, 3B, 4B, 5B, 6B | (POLYMEG) | NG | NG | NG | NG |
| 1C, 2C, 3C, 4C, 5C, 6C | (W-430) | OK | OK | OK | OK |
| 1D, 2D, 3D, 4D, 5D, 6D | (MPT) | NG | NG | NG | NG |
| 1E | (EPAL) | OK | OK | OK | OK |
| 2E | | OK | OK | OK | OK |
| 3E | | OK | OK | NG | NG |
| 4E | | OK | OK | NG | NG |
| 5E | | OK | OK | NG | NG |
| 6E | | OK | OK | NG | NG |

As can be seen from Tables 9 and 10, only the compositions employing m-phenoxybenzyl alcohol were stable through all of the tests.

EXAMPLE 4

Carrier-containing compositions were prepared in the manner described in Example 1 using the ingredients and amounts indicated in Table 11 below wherein the numbers indicate the weight percent of each ingredient based on total composition weight.

TABLE 11

| Sample | OBPA | 2-ethyl hexanol | 2-ethyl-1, 3-hexanediol | DIDP |
|---|---|---|---|---|
| AA | 5 | 20 | — | 75 |
| BB | 5 | — | 20 | 75 |

COMPARATIVE EXAMPLE CC

A solution was prepared in accordance with Example 4, except that 1-decanol was used as the solvent. The 20% OBPA concentrate showed considerable crystallization upon cooling, and the carrier-containing composition showed some OBPA crystals after 1 freeze-thaw cycle and after 7 days room temperature aging. This demonstrates that when the longest continuous chain of carbon atoms in the solvent compound exceeds nine carbon atoms, the stability of the concentrate decreases.

What is claimed is:

1. A homogeneous, stable liquid composition for use in blending with a plastic material comprising a plasticizer for the plastic material, a solvent selected from the group consisting of a branched chain aliphatic alcohols and diols having eight to ten carbon atoms and a 10,10'-oxybisphenoxarsine and present in the composition as a solute in the solvent and constituting greater than 2.5 percent by weight of the combined weight of the plasticizer, solvent and 10,10'-oxybisphenoxarsines.

2. The composition of claim 1 wherein the solvent is isodecyl alcohol.

3. The composition of claim 1 wherein the solvent is 2-ethyl hexanol.

4. The composition of claim 1 wherein the solvent is 2-ethyl-1, 3-hexanediol.

5. The composition of claim 1 wherein the plasticizer is a plasticizer for a vinyl resin.

6. A homogeneous, stable liquid composition for use in protecting plastic products from biological attack comprising a plasticizer for the plastic product, a branched chain aliphatic alcohol or diol solvent having eight to ten carbon atoms, and, present in an amount of at least 4 percent by weight of the total composition, a microbiocidal compound selected from the group consisting of phenoxarsines and phenarsazines present in the composition as a solute in the solvent.

7. The composition of claim 6 wherein the solvent is isodecyl alcohol.

8. The composition of claim 6 wherein the solvent is 2-ethyl hexanol.

9. The composition of claim 6 wherein the solvent is 2-ethyl-1, 3-hexanediol.

10. The composition of claim 6 wherein the solvent 10,10'-oxybisphenoxarsine constitutes from about five to about ten percent by weight of the composition.

11. The composition of claim 10 wherein the solvent is isodecyl alcohol and the phenoxarsine is 10, 10'-oxybisphenoxarsine.

12. The composition of claim 10 wherein the solvent is 2-ethyl hexanol.

13. The composition of claim 10 wherein the solvent is 2-ethyl-1, 3-hexanediol.

* * * * *

UNITED STATES PATENT AND TRADEMARK OFFICE
CERTIFICATE OF CORRECTION

PATENT NO.  : 5,102,657
DATED       : April 7, 1992
INVENTOR(S) : Nuno M. Rei, et al.

It is certified that error appears in the above-identified patent and that said Letters Patent is hereby corrected as shown below:

Claim 1, Col. 14, line 25, strike the "and" after "oxybisphenoxarsine" and before "present".

Claim 6, Col. 14, line 42, change "4" to --5--.

Claim 6, Col. 14, lines 42-44, strike "a microbiocidal compound selected from the group consisting of phenoxarsines and phenarsazines" and substitute --10, 10' oxybisphenoxarsine--

Claim 10, Col. 14, line 52, strike "solvent" at the end of the line.

Signed and Sealed this

Seventh Day of July, 1992

Attest:

DOUGLAS B. COMER

Attesting Officer

Acting Commissioner of Patents and Trademarks